(12) United States Patent
Trovato et al.

(10) Patent No.: US 10,991,264 B2
(45) Date of Patent: *Apr. 27, 2021

(54) MULTI-CAMERA IMAGING FOR IV COMPOUNDING

(71) Applicant: Omnicell, Inc., Mountain View, CA (US)

(72) Inventors: Giuseppe Trovato, Trieste (IT); Andrea Schiavinato, Trieste (IT); Luca Amato, Bolzano (IT)

(73) Assignee: Omnicell, Inc., Mountain View, CA (US)

(*) Notice: Subject to any disclaimer, the term of this patent is extended or adjusted under 35 U.S.C. 154(b) by 13 days.

This patent is subject to a terminal disclaimer.

(21) Appl. No.: 15/865,038

(22) Filed: Jan. 8, 2018

(65) Prior Publication Data

US 2019/0156697 A1    May 23, 2019

(30) Foreign Application Priority Data

Nov. 23, 2017    (IT) .............................. IT2017134813

(51) Int. Cl.
*G09B 19/00* (2006.01)
*G06K 7/10* (2006.01)
(Continued)

(52) U.S. Cl.
CPC .............. *G09B 19/003* (2013.01); *A61J 1/22* (2013.01); *A61J 3/002* (2013.01); *A61M 5/002* (2013.01);
(Continued)

(58) Field of Classification Search
CPC .......... G09B 19/003; A61J 1/22; A61J 3/002; G06K 7/10722; G06K 7/1413; G06T 7/62;
(Continued)

(56) References Cited

U.S. PATENT DOCUMENTS 8,215,557 B1 * 7/2012 Reno ...................... G06M 11/00
235/462.13
8,315,887 B2  11/2012 Berkelhamer et al.
(Continued)

FOREIGN PATENT DOCUMENTS

EP    2 816 346 A1   12/2014
FR       3007611 A1   12/2014
(Continued)

OTHER PUBLICATIONS

"IDS Imaging Development Systems GmbH", data sheet for product No. UI-5481LE-M, Feb. 20, 2017, pp. 1-3. Accessed from the internet: https://en.ids-imaging.com/store/ui-5481le.html.
(Continued)

*Primary Examiner* — John W Miller
*Assistant Examiner* — Humam M Satti
(74) *Attorney, Agent, or Firm* — Kilpatrick Townsend & Stockton LLP

(57) ABSTRACT

Systems and methods for compounding pharmaceuticals, for example for intravenous delivery. The devices include an infrared camera and an infrared light source, and can backlight and photograph items such as syringes in infrared light for enhanced clarity. A visible light camera may also be provided, for example a color digital camera, for documenting other parts of the compounding process. The device may have other sensors, for example a bar code scanner and a weight sensor, for collecting other data about the compounding process. In one example implementation, the device is a compounding assistance device that leads a user of the device through a compounding task using instructions shown on a display. In other implementations, the device may be robotic.

12 Claims, 11 Drawing Sheets
(3 of 11 Drawing Sheet(s) Filed in Color)

(51) Int. Cl.
| | | |
|---|---|---|
| G06T 7/62 | (2017.01) | |
| H04N 5/247 | (2006.01) | |
| H04N 5/225 | (2006.01) | |
| A61M 5/00 | (2006.01) | |
| B65C 9/40 | (2006.01) | |
| G06K 7/14 | (2006.01) | |
| A61J 1/22 | (2006.01) | |
| A61J 3/00 | (2006.01) | |
| G06T 7/70 | (2017.01) | |
| A61M 5/31 | (2006.01) | |
| B65B 3/26 | (2006.01) | |

(52) U.S. Cl.
CPC ............ *B65C 9/40* (2013.01); *G06K 7/10722* (2013.01); *G06K 7/1413* (2013.01); *G06T 7/62* (2017.01); *H04N 5/2256* (2013.01); *H04N 5/247* (2013.01); *A61M 2005/3125* (2013.01); *A61M 2205/3313* (2013.01); *A61M 2205/3393* (2013.01); *A61M 2205/587* (2013.01); *A61M 2205/6072* (2013.01); *B65B 3/26* (2013.01); *B65C 2009/408* (2013.01); *G06T 7/70* (2017.01); *G06T 2207/10024* (2013.01); *G06T 2207/10048* (2013.01)

(58) Field of Classification Search
CPC . G06T 2207/10024; G06T 2207/10048; G06T 7/70; H04N 5/247; H04N 5/2256; A61M 5/002; A61M 2005/3125; A61M 2205/3313; A61M 2205/587; A61M 2205/6072; A61M 2205/3393; B65C 9/40; B65C 2009/408; B65B 3/26
See application file for complete search history.

(56) References Cited

U.S. PATENT DOCUMENTS

| | | |
|---|---|---|
| 8,431,404 B2 | 4/2013 | Spence et al. |
| 8,554,579 B2 | 10/2013 | Tribble et al. |
| 8,639,525 B2 | 1/2014 | Levine et al. |
| 8,666,780 B2 | 3/2014 | Berkelhamer et al. |
| 9,069,887 B2 | 6/2015 | Gupta et al. |
| 9,311,807 B2 | 4/2016 | Schultz et al. |
| 2004/0078231 A1 | 4/2004 | Wilkes et al. |
| 2006/0000470 A1 | 1/2006 | Clarke et al. |
| 2006/0149416 A1 | 7/2006 | Mohapatra et al. |
| 2006/0259195 A1* | 11/2006 | Eliuk ............ B65B 55/16 700/245 |
| 2007/0088590 A1 | 4/2007 | Berkelhamer et al. |
| 2007/0093935 A1 | 4/2007 | Fu |
| 2007/0177778 A1* | 8/2007 | Massaro ............ G01N 35/1016 382/128 |
| 2007/0257192 A1* | 11/2007 | Nishino ............ G01N 21/9505 250/341.4 |
| 2008/0125897 A1 | 5/2008 | Digianfilippo et al. |
| 2008/0140444 A1 | 6/2008 | Karkanias et al. |
| 2008/0195246 A1 | 8/2008 | Tribble et al. |
| 2009/0154764 A1* | 6/2009 | Khan ............ B65B 3/003 382/100 |
| 2009/0188311 A1 | 7/2009 | Cadieux et al. |
| 2009/0198208 A1* | 8/2009 | Stavsky ............ A61J 1/2096 604/407 |
| 2010/0097451 A1* | 4/2010 | Bruce ............ B65B 57/145 348/61 |
| 2010/0118130 A1* | 5/2010 | Harris ............ G01N 21/51 348/61 |
| 2010/0131097 A1* | 5/2010 | Young ............ G01N 21/31 700/244 |
| 2011/0056290 A1* | 3/2011 | Bryant ............ G01F 23/292 73/293 |
| 2011/0211067 A1* | 9/2011 | McKay ............ G01N 21/51 348/135 |
| 2012/0002042 A1 | 1/2012 | Okuma |
| 2012/0173254 A1 | 7/2012 | Korhnak et al. |
| 2012/0173255 A1 | 7/2012 | Korhnak et al. |
| 2012/0199239 A1 | 8/2012 | Okuda et al. |
| 2013/0058550 A1 | 3/2013 | Tanimoto et al. |
| 2013/0142406 A1 | 6/2013 | Lang et al. |
| 2013/0188038 A1 | 7/2013 | Tanimoto et al. |
| 2014/0177932 A1* | 6/2014 | Milne ............ G01N 21/9027 382/128 |
| 2014/0233797 A1 | 8/2014 | Hodder et al. |
| 2014/0350946 A1 | 11/2014 | Klomp |
| 2015/0125945 A1* | 5/2015 | Holmes ............ B04B 5/0414 435/288.7 |
| 2015/0250678 A1 | 9/2015 | Eliuk et al. |
| 2015/0251779 A1 | 9/2015 | Tachibana et al. |
| 2015/0309505 A1 | 10/2015 | Popp |
| 2016/0071265 A1 | 3/2016 | Sandmann et al. |
| 2016/0073019 A1* | 3/2016 | Nowicki ............ G01G 17/00 348/135 |
| 2016/0092639 A1* | 3/2016 | Padmani ............ G06F 21/6245 705/2 |
| 2016/0161402 A1 | 6/2016 | Micheels et al. |
| 2016/0232325 A1 | 8/2016 | Utech et al. |
| 2016/0247277 A1* | 8/2016 | Kriheli ............ B65B 55/02 |
| 2017/0056603 A1* | 3/2017 | Cowan ............ A61M 5/315 |
| 2017/0333623 A1* | 11/2017 | Kamen ............ G06F 19/00 |
| 2018/0008787 A1* | 1/2018 | Schriver ............ A61M 5/2066 |
| 2018/0091745 A1* | 3/2018 | Holmes ............ A61J 1/03 |
| 2018/0108435 A1* | 4/2018 | Brown ............ G01F 23/2921 |
| 2018/0154088 A1* | 6/2018 | Broselow ............ A61M 5/3129 |
| 2019/0041318 A1* | 2/2019 | Wissmann ............ G01N 21/31 |
| 2019/0311490 A1* | 10/2019 | Crawford ............ G06T 7/20 |
| 2020/0261318 A1* | 8/2020 | Ranalletta ............ G16H 40/63 |

FOREIGN PATENT DOCUMENTS

| | | |
|---|---|---|
| JP | 2015-123205 | 7/2015 |
| JP | 2015-167646 A | 9/2015 |
| WO | 2004/053468 A1 | 6/2004 |
| WO | 2012/073774 | 6/2012 |
| WO | 2013/180127 | 12/2013 |
| WO | 2014123147 A1 | 8/2014 |
| WO | 2014/119994 A1 | 8/2016 |
| WO | 2017/116961 a1 | 7/2017 |

OTHER PUBLICATIONS

"Basler dart Area Scan Cameras" brochure, Jan. 2017, pp. 1-8, No. 7. Accessed from the internet: https://www.baslerweb.com/fp-1486541807/media/downloads/documents/brochure/BAS1701_dart_Broschuere_EN_SAP5052_web.pdf.
IT 102017000134813 an Office Action dated Aug. 28, 2018, 11 pages.
PCT/US2018/059641 an International Search Report and Written Opinion dated Mar. 22, 2019, 10 pages.
U.S. Appl. No. 15/827,336 a Non-Final Office Action dated Aug. 7, 2020, 24 pages.
US Appl. No. 16/792,519 a Non-Final Office Action dated Sep. 4, 2020, 8 pages.
PCT/US2018/063493 an International Search Report and Written Opinion dated Feb. 21, 2019, 9 pages.
PCT/US2018/063500 an International Search Report and Written Opinion dated Feb. 7, 2019, 14 pages,

* cited by examiner

MULTI-CAMERA IMAGING FOR IV COMPOUNDING

CROSS-REFERENCE TO RELATED APPLICATIONS

This application claims priority to Italian patent application no. 102017000134813 filed Nov. 23, 2017, the entire disclosure of which is hereby incorporated by reference herein for all purposes.

BACKGROUND OF THE INVENTION

Pharmaceutical compounding is the preparation of patient-specific medications by the processing or combination of ingredients. Many medications, especially medications administered orally in pill form, are now manufactured in a variety of forms and dosages so that little preparation is needed at a pharmacy, other than placing the proper number of pills in a bottle to fill a doctor's prescription for a particular patient. However, medications for intravenous delivery are routinely compounded, for example in hospital pharmacies.

Typically, a physician will prescribe a particular medication or a combination of medications for a specific patient, for intravenous (IV) delivery. The pharmacy receives the prescription and prepares the IV solution with the proper amount of each prescribed medication. The compounded medication is then sent to the hospital floor for administration to the patient.

It is of utmost importance that the correct medications be prepared in the correct proportions, without the introduction of contaminants. Detailed protocols may be developed for the compounder to follow. The number of different protocols may be very large, because there may be a large number of different medications to choose from, in a variety of packages, to be prepared in a number of dosages, and to be provided in a number of different delivery vehicles.

Much of the work of compounding may be delegated to workers who are not registered pharmacists, or to robotic machines. Accordingly meticulous records may be kept of the preparation of each medication, so that the pharmacist can review how each medication was made before it leaves the pharmacy. The records also enable review of the preparation of any particular medication at a later time, should there be any question of its correctness.

BRIEF SUMMARY OF THE INVENTION

According to one aspect, a compounding assistance device comprises a carrier for supporting items. The material of the carrier is not opaque to infrared light. The compounding assistance device further includes an infrared digital camera positioned to photograph at least a portion of the carrier from above. The compounding assistance device further includes an area light source positioned under the carrier. The area light source is configured to generate infrared light and direct the infrared light through the carrier and toward the digital camera. The compounding assistance device further includes a display and a controller. The controller is programmed to guide a user of the compounding assistance device through a pharmaceutical compounding task using one or more prompts shown on the display. In some embodiments, the compounding assistance device further comprises a weight sensor on which the carrier rests, the weight sensor configured to produce a signal indicating the weight of the carrier and any items on the carrier. In some embodiments, the infrared digital camera is a first digital camera, and the compounding assistance device further comprises a second digital camera positioned to photograph at least a portion of the carrier from above, the second digital camera being a visible light camera. The second digital camera may be a color digital camera. In some embodiments, the compounding assistance device further comprises a source of visible light associated with the second digital camera and controllable by the controller to emit light during the taking of a photograph using the first digital camera. In some embodiments, the area light source under the carrier comprises a plurality of infrared light emitting diodes, and a diffuser. In some embodiments, the area light source under the carrier comprises a plurality of infrared light emitting diodes, and the carrier is made of a diffusing material. In some embodiments, the compounding assistance device further comprises a gantry spanning the carrier, and the infrared digital camera is mounted on the gantry. In some embodiments, the compounding assistance device further comprises an adhesive label printer, and the controller is programmed to, upon completion of the pharmaceutical compounding task, print an adhesive label to be affixed to a container holding the pharmaceutical compounded during the compounding task. In some embodiments, the compounding assistance device further comprises a bar code scanner positioned to read a bar code from an item between the bar code scanner and the carrier. In some embodiments, the digital camera is a first digital camera, and compounding assistance device further comprises a second digital camera positioned to photograph at least a portion of the carrier from above, the second digital camera being sensitive to visible light, and a gantry spanning the carrier, wherein the first and second digital cameras and the bar code scanner are mounted on the gantry. In some embodiments, the controller is further programmed to analyze a digital photograph of a syringe taken in infrared light by the digital camera, and estimate an amount of liquid in the syringe based on the analysis of the digital photograph. In some embodiments, the carrier defines a groove of a shape and size for receiving a barrel flange of a syringe. In some embodiments, the controller is further programmed to analyze a digital photograph of a syringe taken in infrared light by the digital camera, recognize a size of the syringe based on the analysis of the digital photograph, and annotate the digital photograph of the syringe with volume indications.

According to another aspect, a method of compounding a medication comprises receiving a syringe into a viewing area between an infrared area light source and an infrared digital camera, taking a digital photograph of the syringe in infrared light using the infrared digital camera, such that the syringe is backlit by the infrared area light source, and storing the digital photograph. In some embodiments, the method further comprises automatically analyzing the digital photograph to compute a volume of liquid in the syringe. In some embodiments, the method further comprises automatically analyzing the digital photograph to ascertain the size and position of the syringe in the digital photograph, and annotating the digital photograph with volume indications. In some embodiments, the infrared area light source and the infrared digital camera are comprised in a compounding assistance device, and receiving the syringe between the infrared area light source and the infrared digital camera comprises receiving the syringe manually from a user of the compounding assistance device. In some embodiments, the compounding assistance device comprises a display and a controller, and the method further comprises leading the user of the compounding assistance device through a compounding task using a series of prompts shown on the display. In some embodiments, the infrared area light source and the infrared digital camera are comprised in a compounding robot, and receiving the syringe between the infrared area light source and the infrared digital camera comprises receiving the syringe from a robotic mechanism. In some embodiments, the digital photograph is a first digital photograph, and the method further comprises taking a second digital photograph of a container involved in the compounding process using a visible light camera, and storing the second digital photograph in association with the first digital photograph. In some embodiments, taking the second digital photograph comprises taking a color photograph.

According to another aspect, a pharmaceutical compounding device comprises an infrared area light source, an infrared digital camera, a viewing area between the infrared area light source and the infrared digital camera, and a controller. The controller is programmed to control the infrared area light source and the infrared digital camera to take a photograph of an item in the viewing area such that the item is backlit by the infrared area light source. In some embodiments, the pharmaceutical compounding device is a compounding assistance device comprising a display, and the controller is further programmed to guide a user of the device through a compounding task using prompts shown on the display. In some embodiments, the pharmaceutical compounding device is a compounding robot. In some embodiments, the pharmaceutical compounding device further comprises a visible light camera under the control of the controller.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
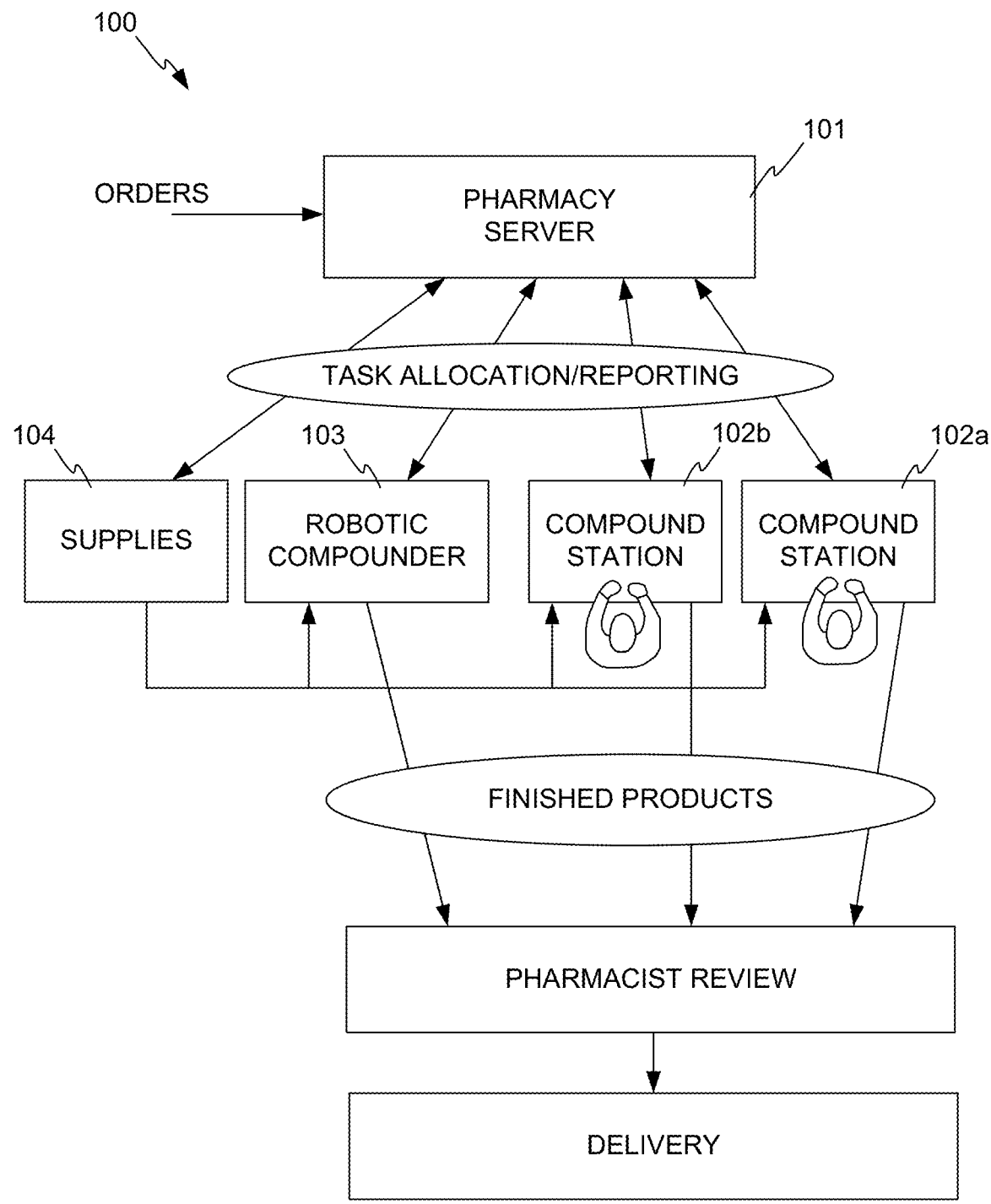
FIG. 1 illustrates a compounding pharmacy in accordance with embodiments of the invention.

FIG. 1 illustrates a compounding pharmacy 100 in accordance with embodiments of the invention. The operation of pharmacy 100 is coordinated by a pharmacy server 101, described in more detail below. Pharmacy server 101 receives orders for compounded medications, for example prescriptions from physicians. Pharmacy server 101 maintains extensive records of orders received, detailed protocols for the compounding of medications, records of the preparation of medications in response to orders, and other items. Pharmacy server 101 also allocates tasks to one or more compounding stations, which may include manual compounding stations such as stations 102a and 102b, and one or more robotic compounders 103. The compounding stations may also report information to pharmacy server 101, for example records of the compounding of each ordered medication.

Working materials are supplied to the compounding stations from a supply store 104. Pharmacy server 101 may maintain an inventory of the materials in supply store 104, and may track the movements of medications and supplies within pharmacy 100.

Finished products are reviewed by the pharmacist and delivered from pharmacy 100 to their points of use, for example patient rooms for administration by a nurse to a patient. It will be understood that the above description is highly generalized, and that a working compounding pharmacy may have many other systems and facilities.

Figure 2:
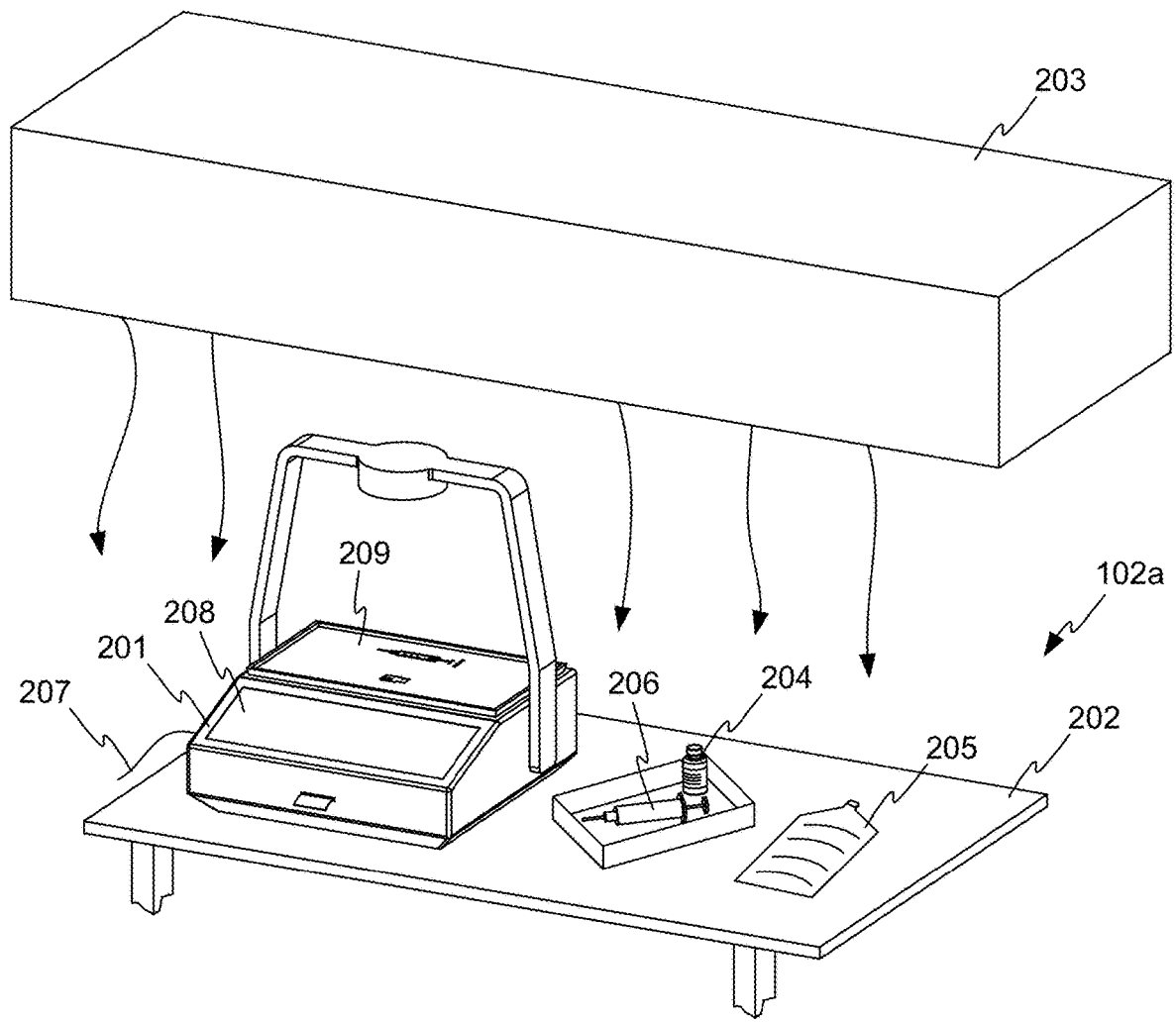
FIG. 2 illustrates a manual compounding station in accordance with embodiments of the invention.

FIG. 2 illustrates a manual compounding station 102a in accordance with embodiments of the invention. Compounding station 102a includes a compounding assistance device 201 on a surface 202. Compounding assistance device 201 may be placed under a laminar flow hood 203, which flows filtered air over compounding assistance device 201 and surface 202, to help avoid contamination of the materials being worked on, and for protection of the user of compounding station 102a.

In the example shown, compounding station 102a has received supplies for a simple compounding task. A medication supplied in a vial 204 is to be added to an IV drip bag 205. A syringe 206 may be used to accomplish the transfer.

Compounding assistance device 201 has several features and capabilities that will assist the compounder in properly preparing the formulation in IV drip bag 205, and in thoroughly documenting the process. Compounding assistance device 201 has a network connection 207 to pharmacy server 101, though which compounding assistance device 201 may receive a protocol from pharmacy server 101 describing the steps required to perform the compounding task.

Compounding assistance device 201 includes a display screen 208 on which instructions to the user may be presented or through which the user may input information. For example, display screen 208 may be a touchscreen display, sensitive to touch and able to distinguish the location of a touch. Compounding assistance device 201 also includes a tray 209 which provides a carrier for holding items while they are weighed or photographed, as is described in more detail below.

Figure 3:
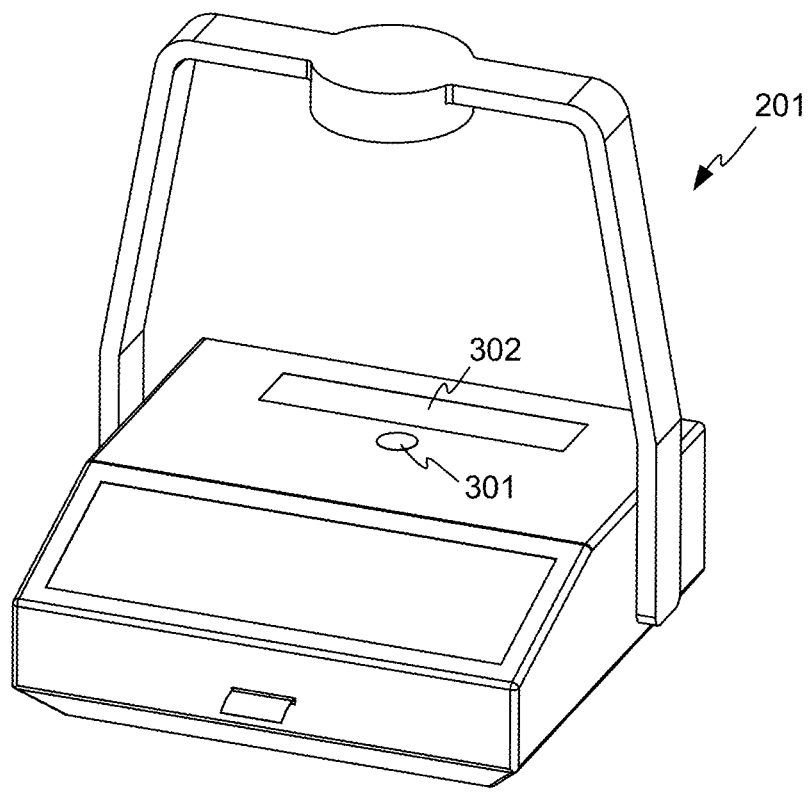
FIG. 3 shows a compounding assistance device, in accordance with embodiments of the invention.

FIG. 3 shows compounding assistance device 201, with tray 209 removed, in accordance with embodiments of the invention. Visible in FIG. 3 is a weight sensor 301, for example a load cell, for weighing tray 209 and its contents. Also visible is an area light source 302. Area light source 302 is a two-dimensional extended or area light source, and emits light from many points or continuously across its face. Area light source 302 may be, for example, an infrared light panel, illuminating a portion of tray 209 from below with infrared light.

Figure 4:
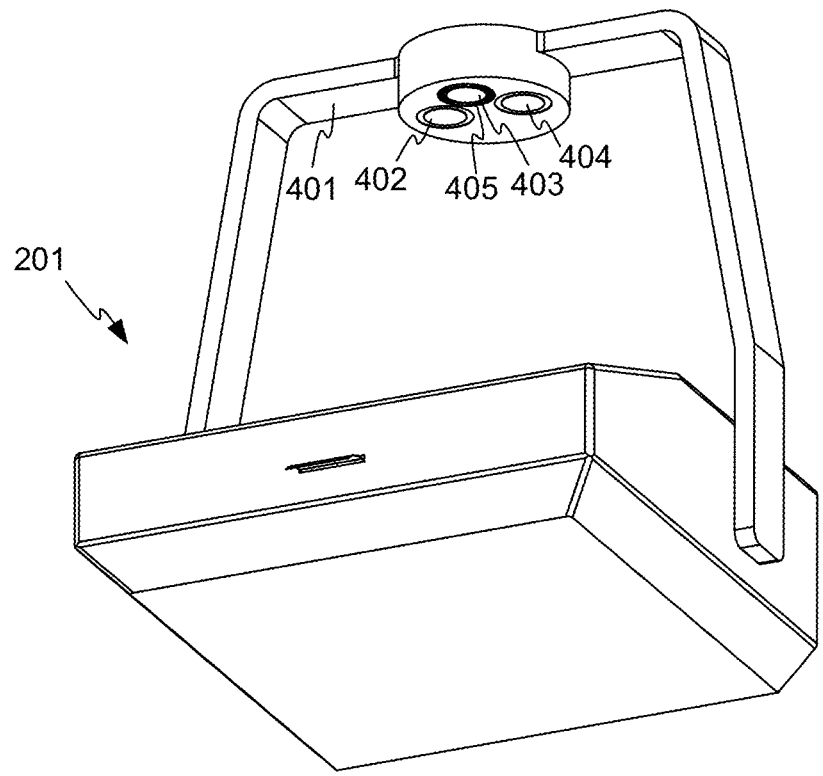
FIG. 4 shows a lower oblique view of the compounding assistance device of FIG. 3, in accordance with embodiments of the invention.

FIG. 4 shows a lower oblique view of compounding assistance device 201, in accordance with embodiments of the invention. A gantry 401 spans tray 209. Positioned on gantry 401 are a bar code scanner 402, a visible light camera 403, and an infrared camera 404. Visible light camera 403 may further include one or more light sources 405 for illuminating at least a portion of tray 209 from above. Light sources 405 may be, for example, one or more white-light light emitting diodes (LEDs) surrounding visible light camera 403, or another kind of light source. For the purposes of this disclosure, light is "visible" if it includes light wavelengths between about 400 and 700 nanometers. Light is "white" if it includes enough wavelengths in the visible range to enable reasonably complete color recognition.

The area above tray 209 may be called a viewing area for items to be photographed by infrared camera 404 or visible light camera 403, or scanned by bar code scanner 402. In other embodiments, an item may not necessarily be lit from below and photographed from above. For example, in a compounding robot, a robotic mechanism may hold an item to be photographed in the field of view of a camera in any orientation. For example, an item may be photographed from below, or horizontally.

Bar code scanner 402 is positioned to read bar codes on items held in the viewing area between tray 209 and bar code scanner 402. Visible light camera 403 and infrared camera 404 are position to take photographs of items on tray 209.

During compounding of a medication one or more of weight sensor 301, bar code scanner 402, visible light camera 403, and infrared camera 404 can be used to provide documentation of how the medication was compounded, and to avoid errors.

For example, to perform the compounding task illustrated in FIG. 2, pharmacy server 101 sends detailed sequential instructions to compounding assistance device 201, which then leads the user through the steps required to formulate the specific medication in the specific dose required, for delivery in the specific delivery vehicle. In this example, the task may involve transferring 30000 units of Heparin (a common anticoagulant) from a vial containing 5000 units/ml of Heparin in solution, to an IV drip bag. The volume of solution required for transfer is therefore 6 ml. Vial 204 and IV drip bag 205 have been supplied to compounding station 102a, along with syringe 206, which will be needed to make the transfer.

Figure 5:
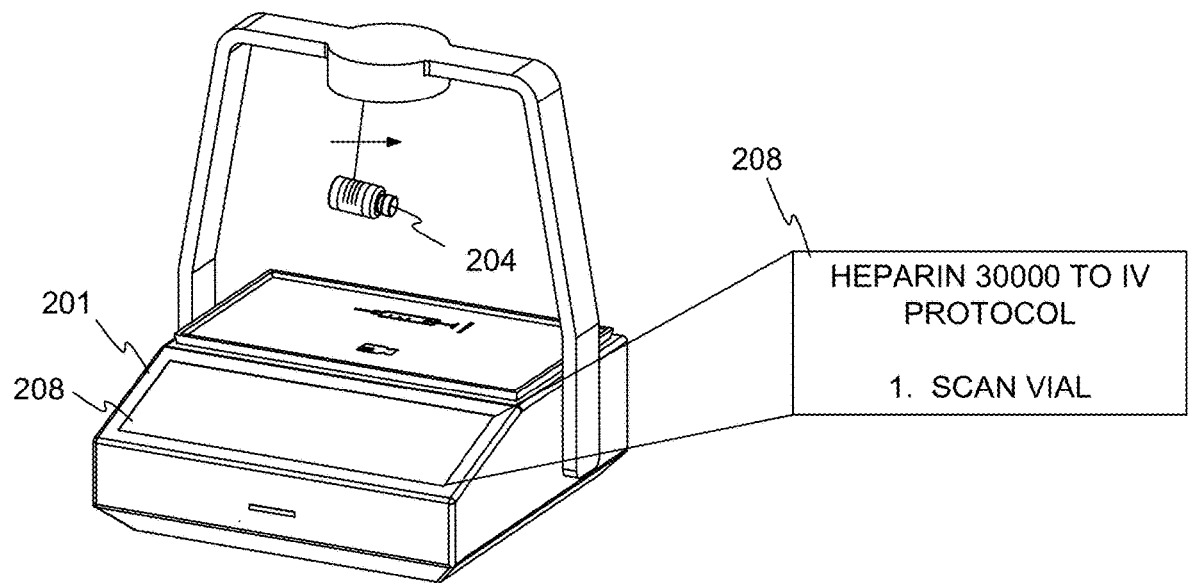
FIG. 5 illustrates bar code scanning by the compounding assistance device of FIG. 3, in accordance with embodiments of the invention.

First, compounding assistance device 201 requires that the user present vial 204 to bar code scanner 402, so that the identifying bar code on vial 204 can be read, and the system can verify that the correct vial with the correct concentration has been provided. If not, then an error message is generated and the compounding task is stopped. The scanning process is illustrated in FIG. 5, along with an example prompt shown on screen 208. Compounding assistance device 201 may automatically recognize that the barcode has been detected, and may move to the next step. Alternatively, an acknowledgment from the user may be required, in this and other steps.

Figure 6:
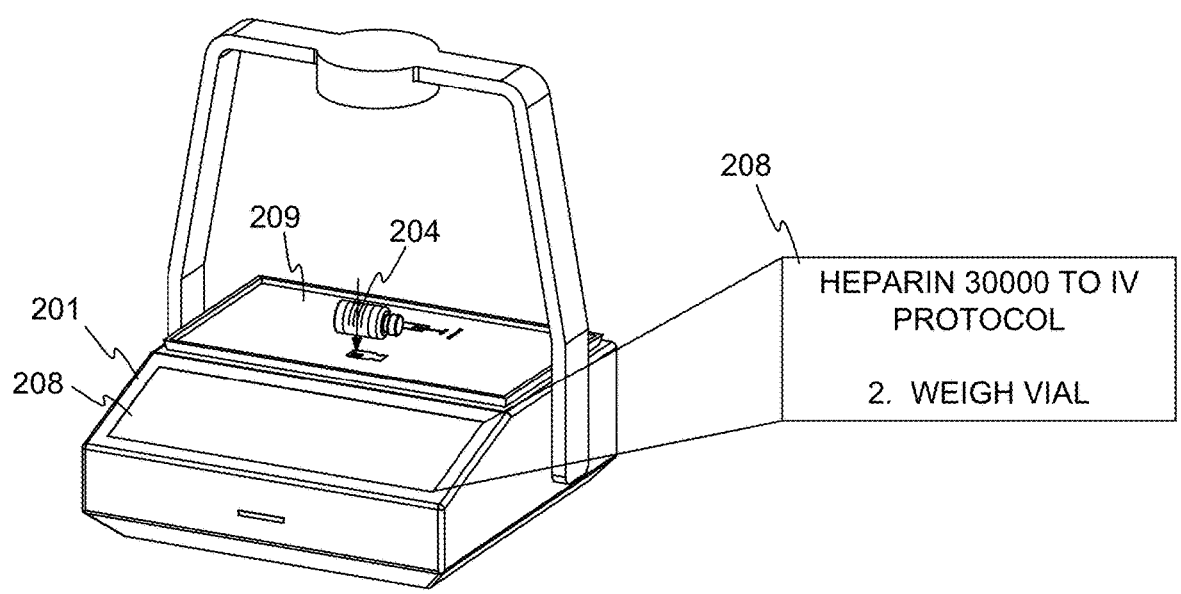
FIG. 6 illustrates a step in a compounding process, in accordance with embodiments of the invention.

FIG. 6 illustrates a second step in the compounding process, in which an initial weight of vial 204 is collected. For this purpose, vial 204 is placed on tray 209. Tray 209 may include an icon 601 indicating where vial 204 should be placed, and may also include mechanical features for aiding in proper placement of vial 204. For example, a gently V-shaped trough may be formed into tray 209. Compounding assistance device 201 may automatically recognize the weight of vial 204 on tray 209, record the weight, and move to then next step of the compounding process.

In some embodiments, vial 204 may also be photographed while on tray 209 using visible light camera 403, using ambient light, light from light sources 405, or a combination thereof.

Figure 7:
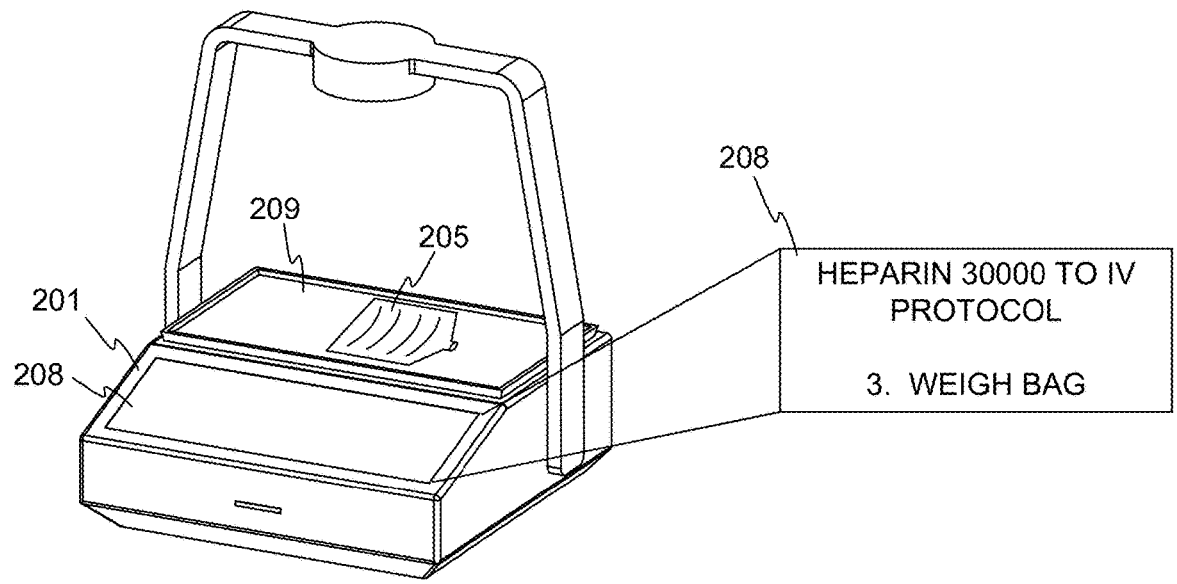
FIG. 7 illustrates another step in the compounding process, in accordance with embodiments of the invention.

FIG. 7 illustrates a third step, in which an initial weight of IV bag 205 is collected. Compounding assistance device 201 may then prompt the user to draw the correct amount (6 ml) of solution from vial 204 into syringe 206.

Figure 8:
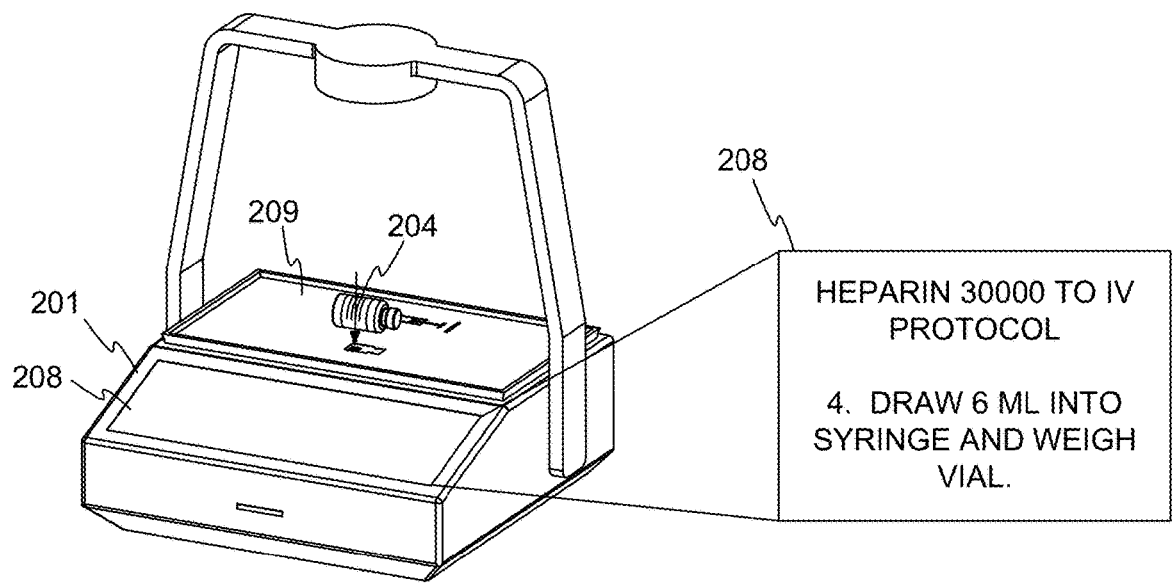
FIG. 8 illustrates another step in the compounding process, in accordance with embodiments of the invention.

FIG. 8 illustrates a fourth step, in which an after-drawn weight of vial 204 is taken, in a manner similar to the taking of the initial vial weight shown in FIG. 6. The system can compare the two weights of vial 204 to calculate the amount of solution drawn from vial 204, for recordkeeping and for verification that the proper amount of solution was drawn.

Figure 9:
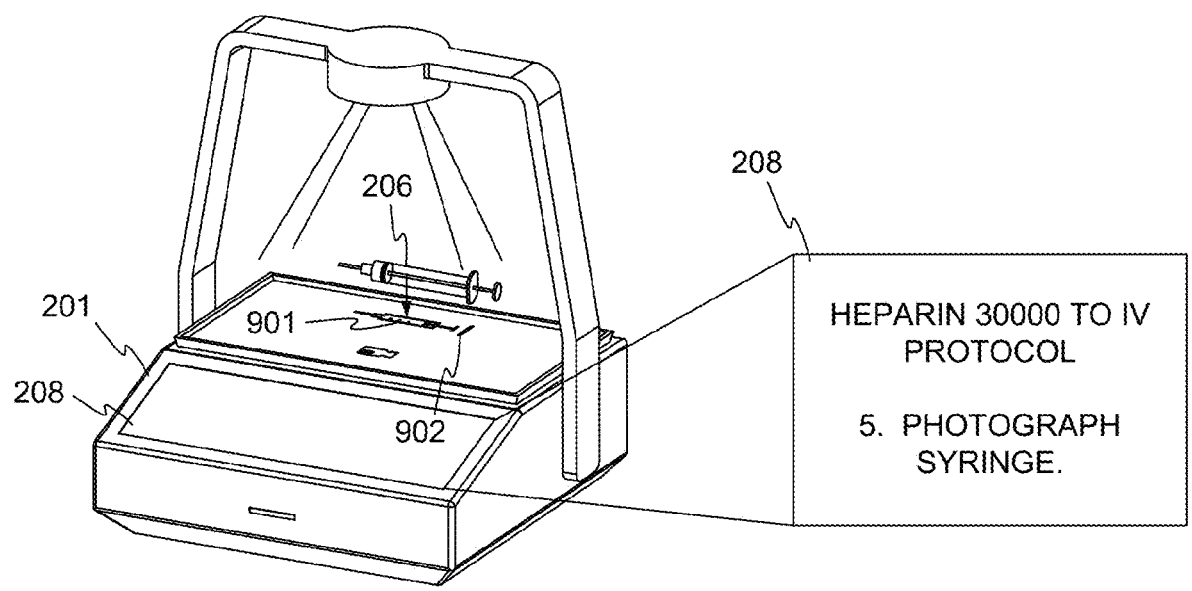
FIG. 9 illustrates another step in the compounding process, in accordance with embodiments of the invention.

FIG. 9 illustrates a fifth step, in which the filled syringe is photographed. For this purpose, tray 209 may include an icon 901 for placement of syringe 206, and may include mechanical features facilitating correct placement and alignment of syringe 206 on tray 209, for example a V-shaped trough, or a groove 902 shaped and sized to receive an edge of the barrel flange of syringe 206. Other fiducial marks may be present as well.

Figure 10:
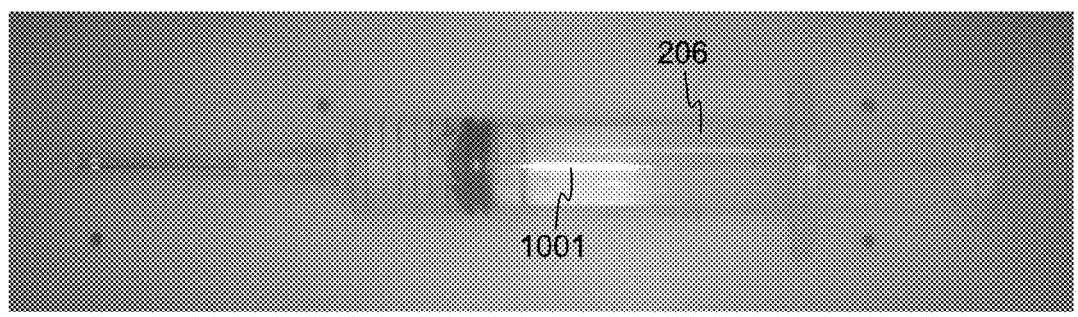
FIG. 10 shows a photograph as may be taken using a visible light camera, in accordance with embodiments of the invention.

Syringe 206 may be photographed using visible light camera 403, but is preferably photographed using infrared camera 404. FIG. 10 shows a photograph as may be taken using visible light camera 403. (Visible light camera 403 preferably has a field of view larger than shown in FIG. 10, but syringe 206 has been isolated from the larger view for ease of explanation.) While syringe 206 is readily visible in the photograph of FIG. 10, the photograph has been affected by glare spot 1001, and may have been affected by ambient light sources that are not under the control of compounding assistance device 201.

Figure 11:
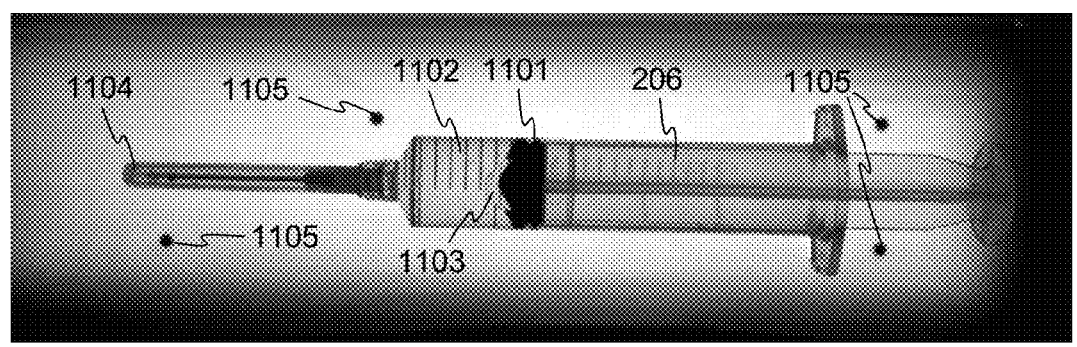
FIG. 11 shows a photograph of a syringe as may be taken using an infrared camera, in accordance with embodiments of the invention.

FIG. 11 shows a photograph of syringe 206 as may be taken using infrared camera 404. Tray 209 is not opaque to infrared radiation, so syringe 206 is backlit by infrared light source 302. For example, tray 209 may be substantially transparent to infrared radiation, or may be translucent. In some embodiments, tray 209 may be made of polycarbonate or another suitable polymer or blend of polymers. Infrared camera 404 may have a wavelength-selective optical filter that passes infrared light to camera 404, but blocks the visible spectrum. Thus, glare spots formed from visible light are excluded from the photograph of FIG. 11, resulting in greater clarity of features of syringe 206.

Whichever kind of camera is used, compounding assistance device 201 can automatically analyze the resulting photograph for any of a number of purposes. For example (referring to FIG. 11), the position of the plunger 1101 of syringe 206 may be automatically recognized, and the amount of drawn liquid 1102 calculated based on the known dimensions of syringe 206. In some embodiments, bubbles such as bubble 1103 may be detected and flagged if they are large enough to significantly affect the dose of medication being prepared. In some protocols, the weight of syringe 206 before and after drawing liquid from vial 204 may be used to verify that the correct amount of liquid was placed into syringe 206. In that case, compounding assistance device 201 may also photograph syringe 206 at each weighing and analyze the photographs to detect whether syringe cap 1104 may have been mistakenly included in one weighing but not another. Fiducial marks 1105 on tray 209 are placed in known positions, and may be detected in the photograph and used to calibrate distances in the photograph.

Figure 12:
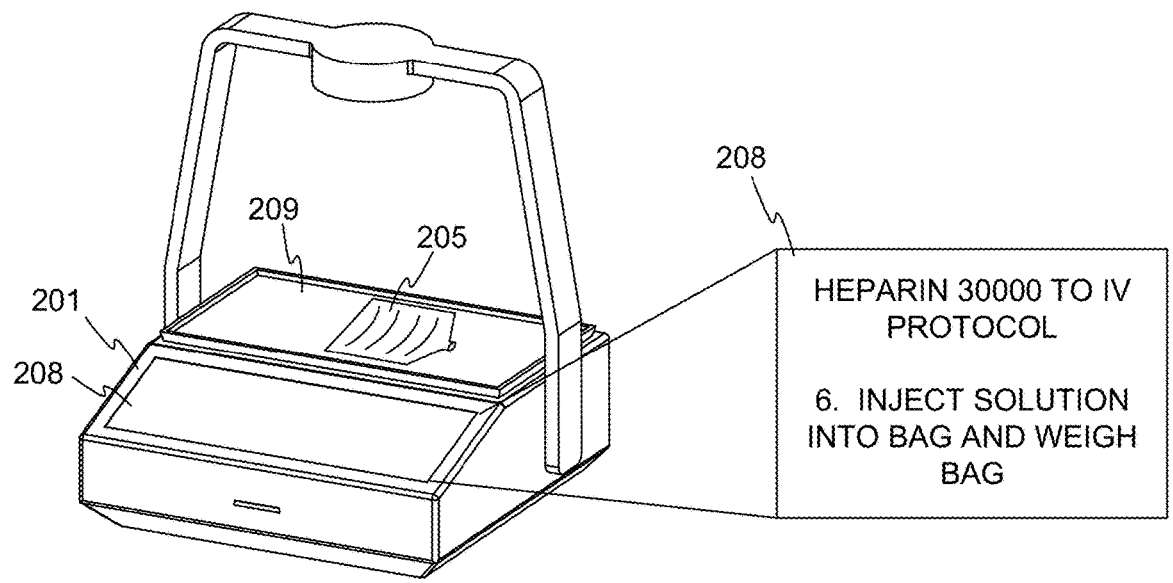
FIG. 12 illustrates another step in the compounding process, in accordance with embodiments of the invention.

FIG. 12 illustrates a sixth step, in which IV bag 205 is re-weighed after addition of solution from syringe 206. Compounding assistance device 201 can compare the before and after weights of bag 205 to verify that the correct amount of Heparin solution was placed into bag 205.

Figure 13:
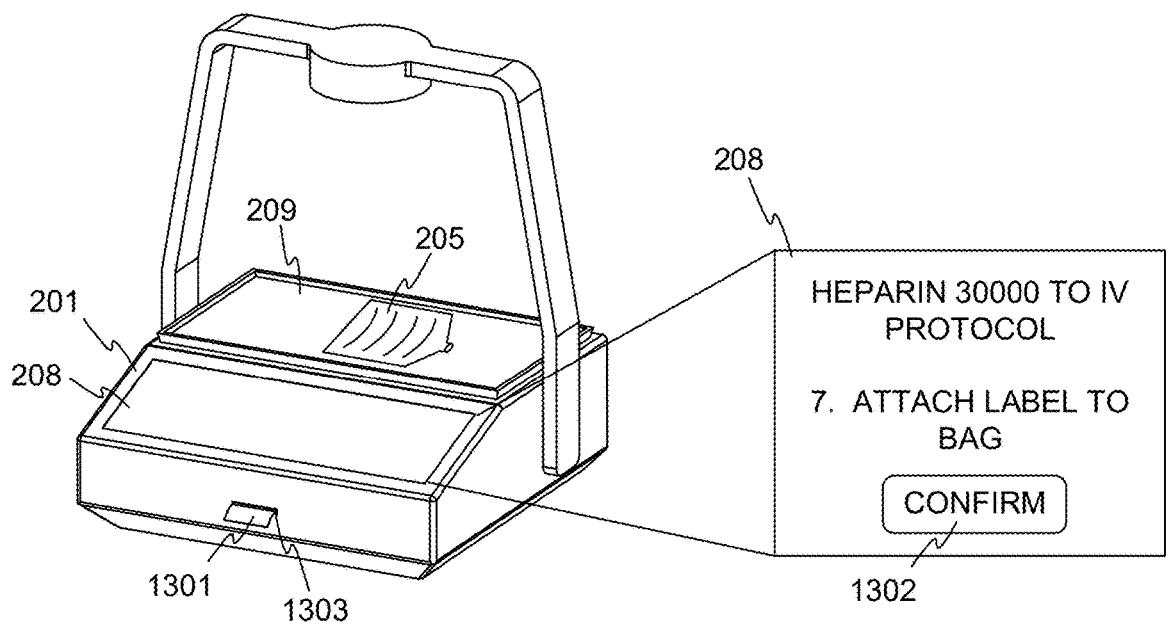
FIG. 13 illustrates another step in the compounding process, in accordance with embodiments of the invention.

FIG. 13 illustrates a seventh step, in which (presuming all of the checks in the system have verified that the compounding process was done correctly) compounding assistance device 201 prints a label 1301 using label printer 1303, to be placed on bag 205, and the user is prompted to adhere label 1301 to bag 205. The finished medication can then be delivered to its point of use, and any consumable items disposed of, for example syringe 206. The user may be asked to confirm 1302 that label 1301 has been affixed, using display 208. In some embodiments, a final photograph of completed bag 205 may be taken for pharmacist review.

The compounding process described above is but one example, and many different compounding workflows may be implemented that have different steps, that use different medication containers, that collect different or additional information for process verification, or that differ in other ways from the example shown.

While the above example was shown in the context of compounding workstation 102a, a similar process may be followed for compounding using a robotic compounder such as robotic compounder 103 shown in FIG. 1. A robotic compounder is a machine, usually enclosed, that use a robotic mechanism to handle vials, syringes, bags, and the like to prepare compounded medications. A robotic compounder may include a scale, one or more cameras, agitation devices, disposal ports, material and supply loading windows, and a delivery window for delivering a finished medication. Robotic compounders are not subject to human error in the compounding process, but include various weight and photographic checks on their work to guard against improper loading of materials, mechanical malfunctions, programming errors, and the like.

Whether compounding is done manually or robotically, the data collected during the compounding process is stored, for example on pharmacy server 101, and can be reviewed by the responsible pharmacist. For example, the pharmacist can verify that the correct kind of vial containing the correct medication was identified by the barcode scan. The dosage can be verified by looking at the photograph of the syringe, the before and after weights of the vial, the before and after weights of the bag, or any combination of these. Any digital photographs taken during the compounding process may be made available for inspection by the pharmacist. For example, the pharmacist may look at a photograph such as the photograph of FIG. 11 to determine whether excessive bubbles may have been included in the liquid drawn into syringe 206.

Upon completion of the compounding task, pharmacy server 101 may assign another compounding task to compounding station 102a, and download another protocol to compounding assistance device 201 in accordance with the new task.

Figure 14:
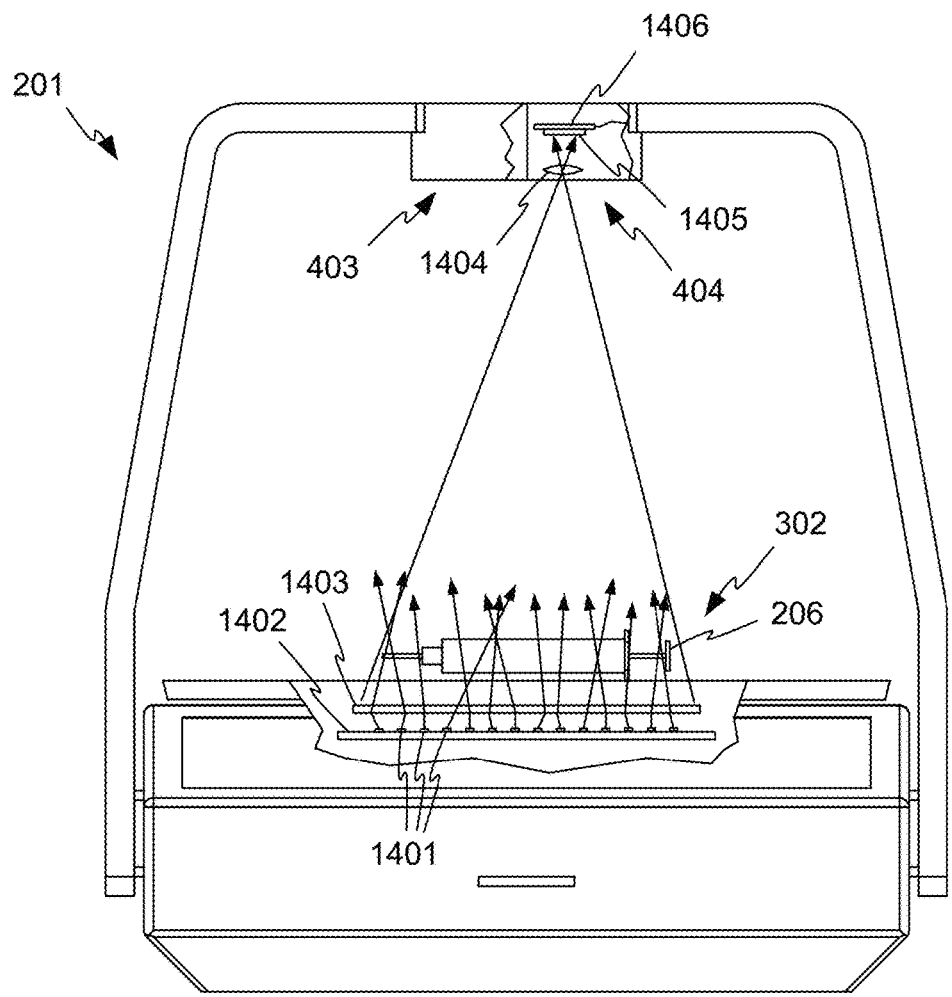
FIG. 14 illustrates the arrangement of an area light source and an infrared camera of the compounding assistance device of FIG. 3, in an embodiment of the invention.

FIG. 14 illustrates the arrangement of area light source 302 and infrared camera 404 of compounding assistance device 201, in an embodiment of the invention.

In this example, area light source 302 includes an array of infrared light emitting diodes (LEDs) 1401 mounted to a circuit board 1402. Light from infrared LEDs 1401 passes through a diffuser 1403, and is scattered upward. Some of the light reaches a lens 1404 of infrared camera 404, which forms an image onto an electronic array light sensor 1405, which in turn is mounted on a printed circuit board 1406. Printed circuit board 1406 may interface with a controller within compounding assistance device 201, to receive signals for controlling electronic array light sensor 1405.

Infrared LEDs 1401 may emit light in the near infrared wavelengths, for example between about 700 and 900 nanometers. In other embodiments, other wavelengths may be used. Diffuser 1403 provides a generally uniform backlight for items placed on area light source 302, for example syringe 206. Area light source 302 may be controlled by an electronic controller within compounding assistance device 201. In some embodiments, tray 209 may be made of a diffusing material, and may be used in addition to or instead of diffuser 303 to diffuse the light from area light source 302.

In other embodiments, other kinds of light sources may be used, for example an edge-lit light guide plate having scattering features on one side. In this arrangement, light sources direct light into one or more edges of the light guide plate, and the light propagates by total internal reflection within the plate until it strikes one of the scattering features. Some of the scattered light is scattered out of the side of the plate opposite the scattering features. The scattering features are preferably distributed so that the intensity of the light exiting the plate is substantially uniform across the area of the plate. A diffuser may also be used to further diffuse the light exiting the plate, for additional uniformity in brightness.

Electronic array light sensor 1405 may be, for example, a charge coupled device (CCD) sensor, a complementary metal oxide semiconductor (CMOS) sensor, or another suitable kind of sensor. In general, such sensors exploit the property of some semiconductor materials that when the material is struck by light, free electrons are generated in proportion to the intensity of the light. The sensor is divided into specific light-sensitive areas called "pixels". To capture an image, the pixels are reset and then exposed to light for an exposure time. At the end of the exposure time, the amount of charge accumulated in each pixel is measured and converted to a numerical value. An array of these numerical values may be called a "digital image", with each value in the array representing the brightness of the light falling on the corresponding pixel.

In a CCD sensor, the accumulated charges are shifted off of the sensor to a charge amplifier, the output of which is digitized for each pixel. In a CMOS sensor, the accumulated charge can be read from each pixel directly, without shifting.

Electronic array light sensor 1405 may have any number of pixels sufficient to resolve features of interest at tray 209. In some embodiments, electronic array light sensor 1405 may include an array 2560×1920 pixels, or about five megapixels. Other array sizes may be used in other embodiments. Electronic array light sensor 1405 is sensitive to light in the infrared wavelengths emitted by area light source 302, For example, electronic array light sensor 1405 may be a silicon-based sensor sensitive to near infrared light. Infrared camera 404 may include an optical filter (not shown) that excludes other wavelengths. The optical filter may be, for example, a dichroic filter that passes light in the wavelengths of interest, but blocks light in other wavelengths, for example visible light.

As is explained above, infrared camera 404 can produce photographs of items on tray 209 that may be clearer in some aspects relevant to pharmaceutical compounding than photographs taken using visible light camera 403. For example, glare spots caused by ambient room light can be largely eliminated. This clarity facilitates analysis of the digital photographs taken using infrared camera 404 for measurement and annotation that may be helpful to a reviewing pharmacist.

Figure 15:
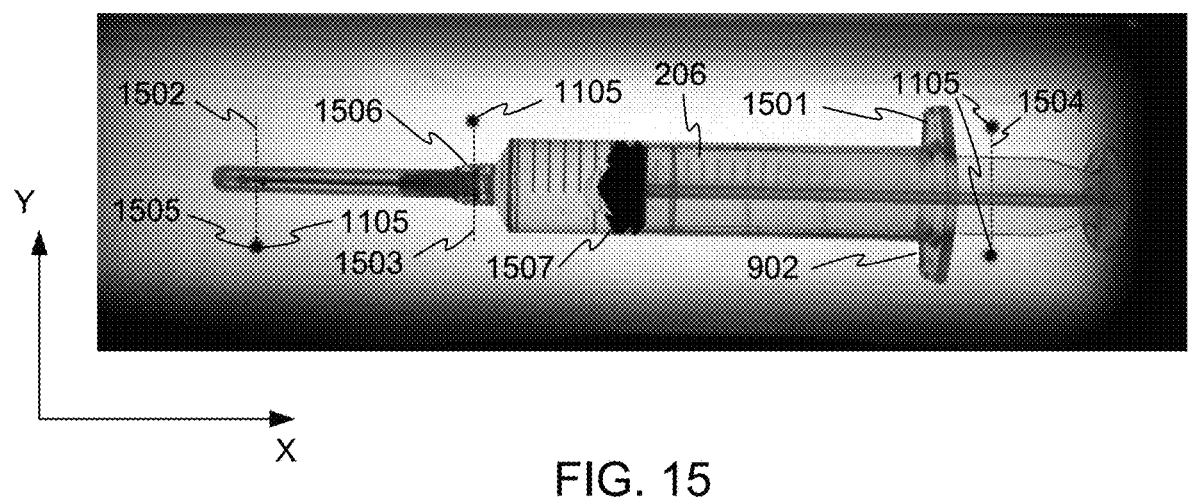
FIG. 15 shows a photograph similar to the photograph of FIG. 11, taken using an infrared camera, and illustrating image analysis in accordance with embodiments of the invention.

FIG. 15 shows a photograph similar to the photograph of FIG. 11, taken using an infrared camera such as infrared camera 404, and illustrating image analysis in accordance with embodiments of the invention. The controller within compounding assistance device 201 may "know" the relative positions of fiducial marks 1105, as measured in image pixels, based on the known locations of fiducial marks 1105 on tray 209, the number of pixels in electronic image sensor 1405, and the magnification of the optical system including lens 1404. The controller can quickly locate the fiducial marks in the image by looking for a pattern of dark spots near the expected locations of the fiducial marks in the image. The pixel locations of the fiducial marks in the image may be recorded for reference.

As is visible in FIG. 15, barrel flange 1501 of syringe 206 has been placed in groove 902 of tray 209, and thus barrel flange 1501 is precisely located with respect to fiducial marks 1105 in the "X" direction shown in FIG. 15. The controller may then query the brightness values of the pixels in the image near the fiducial marks, to locate edges of syringe 206 in the "Y" direction. For example, pixels along column lines 1502, 1503, and 1504 may be analyzed, looking for abrupt light-to-dark and dark-to-light transitions that indicate the presence of edges of parts of syringe 206.

Figure 16:
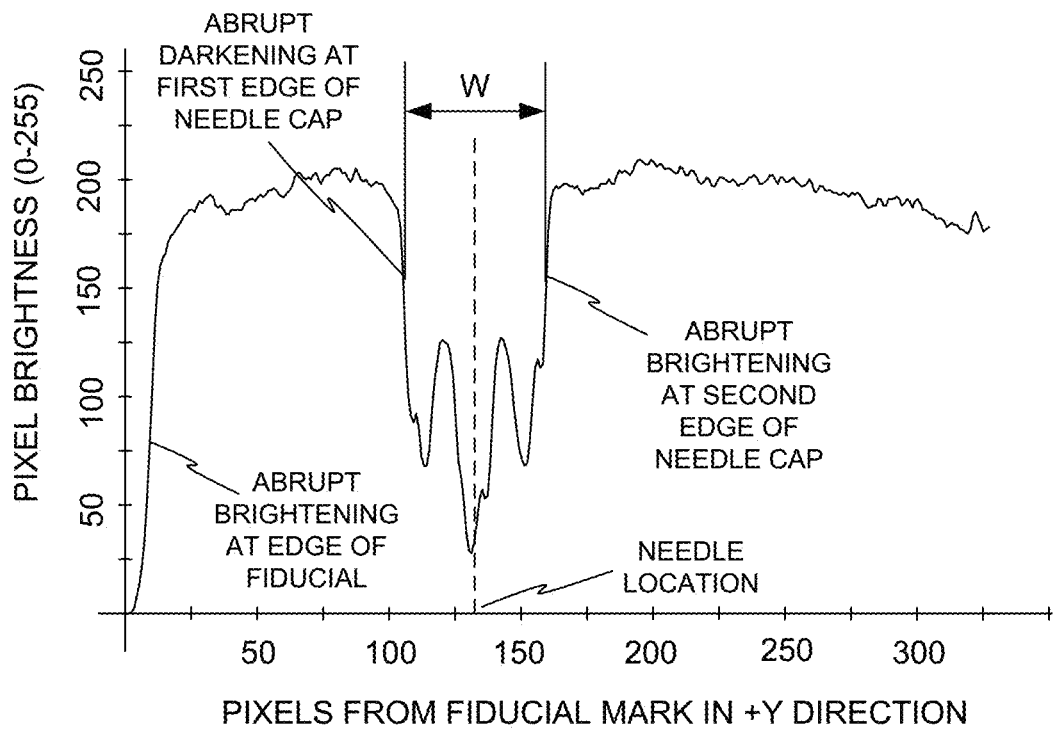
FIG. 16 illustrates an example of a trace of the brightness of pixels along a column line in the image of FIG. 15, in accordance with embodiments of the invention.

FIG. 16 illustrates an example of a trace of the brightness of pixels along column line 1502, moving in the +Y direction from lower left fiducial mark 1505. The transitions spanned by width W may be presumed to include be the needle of syringe 206. If no drop in brightness is detected at the expected location of the needle, then the controller may consider that no needle is attached to syringe 206. Presuming a drop is detected, then the centerline of the region spanned by width W may be presumed to be the centerline of the needle. The width W may be compared with known dimensions of the parts of syringe to determine whether a cap is present on the needle.

Referring again to FIG. 15, similar traces may be performed along other lines to detect the presence and size of a luer lock 1506, or the presence and size of a plunger (not labeled) of syringe 206. The detected dimensions may be compared with stored dimensions of standard syringes, so that the size of syringe 206 is automatically determined.

In other embodiments, other image processing techniques may be used to ascertain the location and size of a syringe from a digital image. For example, a correlation operation may be performed with a previously-prepared syringe photograph. The previous photograph may be compared with the current photograph in a number of orientations and positions, to find the location that best correlates with the syringe in the current photograph, to ascertain the location of the syringe in the current photograph. Fiducial marks 1105 may be found in this way as well. In other embodiments, a synthetic syringe image may be used in the correlation operation. Many other techniques are possible.

Once the size and location of syringe 206 are known in pixel space, the controller may annotate the digital image of the syringe, to assist the pharmacist in reviewing the compounding operation in which the image was taken.

In some embodiments, similar image processing techniques may be used to locate plunger 1507 in the digital image. Given the location of plunger 1507, the location and orientation of syringe 206, and the size of syringe 206, an estimate of the volume of liquid in syringe 206 can be computed.

Figure 17:
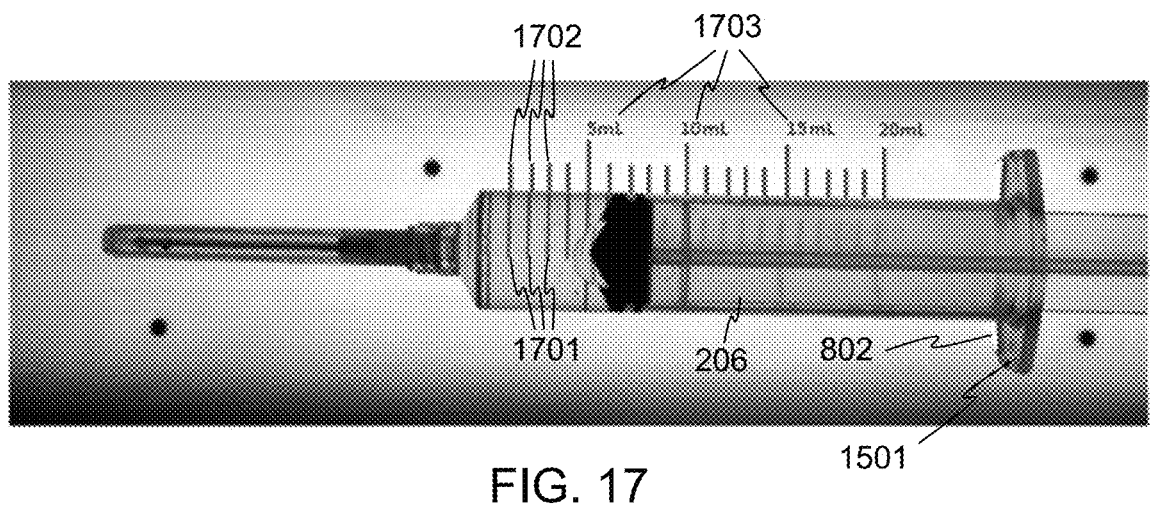
FIG. 17 illustrates a way of annotating an infrared image, in accordance with embodiments of the invention.

FIG. 17 illustrates one way of annotating an infrared image, in accordance with embodiments of the invention. Once the size and location of syringe 206 have been ascertained, the size can be correlated to a standard syringe having pre-recorded measurements, including the locations of gradation marks 1701 on the syringe barrel indicating volumes of liquid in the syringe based on plunger position. While gradation marks 1701 are highly visible in FIG. 17, this may not always be the case. Depending on the positioning of the syringe on tray 209, gradation marks 1701 may not be readily visible in any images. For example, syringe 206 may have been placed on tray 209 with gradation marks 1701 facing downward, or the liquid within syringe 206 may be opaque, hiding gradation marks 1701.

Using the known size and position of syringe 206, compounding assistance device 201 can annotate images taken by either of its cameras to enhance the readability of the plunger position. In FIG. 17, compounding assistance device has altered some of the pixels of the image to show lines 1702 corresponding to the computed locations of gradation marks 1701, and has also added text 1703 showing the liquid volumes represented by lines 1702. In other embodiments, other kinds of annotation may be provided, for example using different colors.

Figure 18:
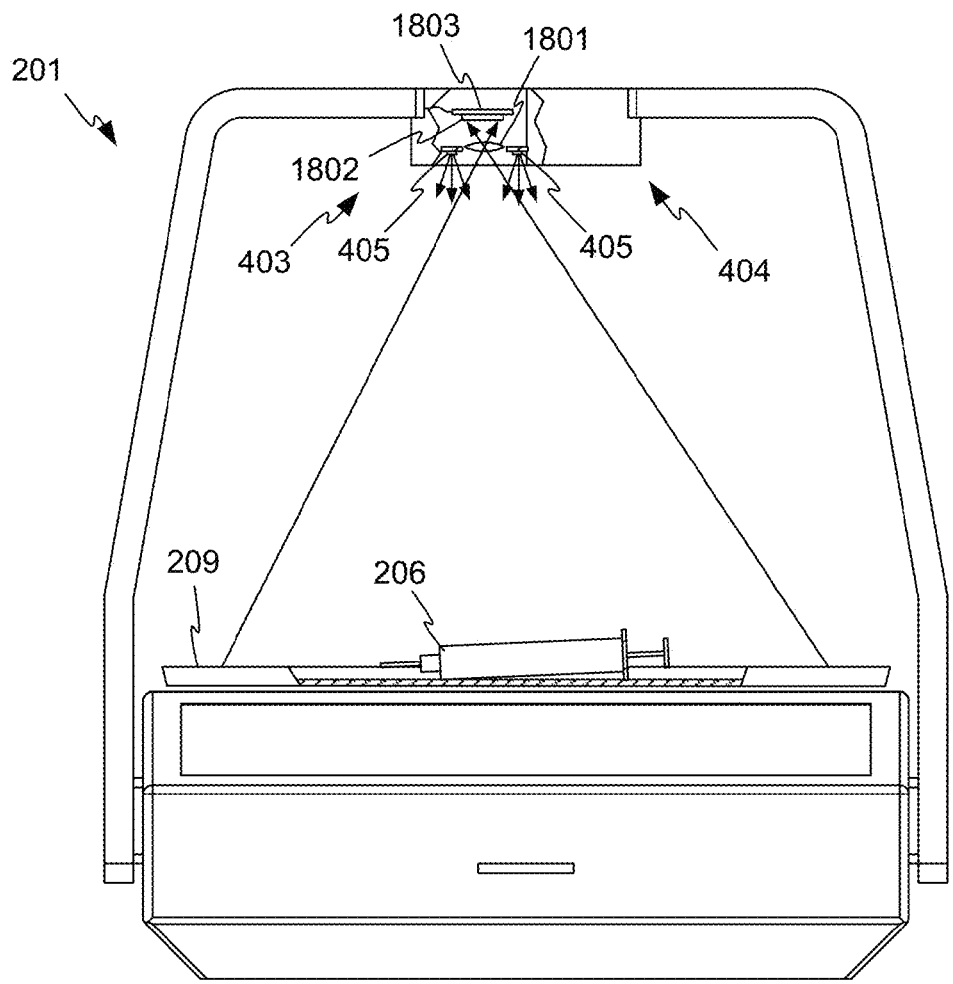
FIG. 18 illustrates the arrangement of a visible light camera in the compounding assistance device of FIG. 3, in an embodiment of the invention.

FIG. 18 illustrates the arrangement of visible light camera 403 of compounding assistance device 201, in an embodiment of the invention. Visible light camera 403 may be used to photograph items on tray 209, for verification that the correct ingredients were used in a compounding task, for final verification that the resulting product looks as it should, or for other purposes. Visible light camera 403 may be a color camera, and may be especially useful for recording the color of a formulation as additional verification that the formulation is likely correct. (Example infrared camera 404 as described above cannot distinguish color due to the narrow band of infrared wavelengths it records and the lack of any color filters on its pixels.)

Visible light camera 403 includes a lens 1801 that focuses light received within its field of view onto an electronic sensor array light sensor 1802, which is in turn mounted on a printed circuit board 1803. Visible light camera 403 may include an optical filter (not shown) such as a dichroic filter that substantially prevents infrared wavelengths from reaching sensor 1802. Light sources 405 may be used to supplement any ambient light illuminating tray 209. For example, light sources 405 may be white LEDs directed at tray 209, and controllable by the controller within compounding assistance device 201.

Electronic array light sensor 1802 may be a CCD sensor, a CMOS sensor, or another suitable kind of sensor as described above, having enough pixels to resolve features of interest at tray 209. For example, sensor 1802 may include an array 2560×1920 pixels, or about five megapixels. Other sensor sizes may be used. Sensor 1802 preferably includes color filters placed over individual pixels so that visible light camera 403 can record color images. For example, sensor 1802 may include red, green, and blue filters in the well-known Bayer pattern.

Visible light camera 403 and infrared camera 404 may be provided as pre-assembled camera modules that include standard interfaces for control by compounding assistance device 201. Suitable camera modules are available from Basler AG of Ahrensburg, Germany, and IDS Imaging Development Systems GmbH of Obersuim, Germany.

Figure 19:
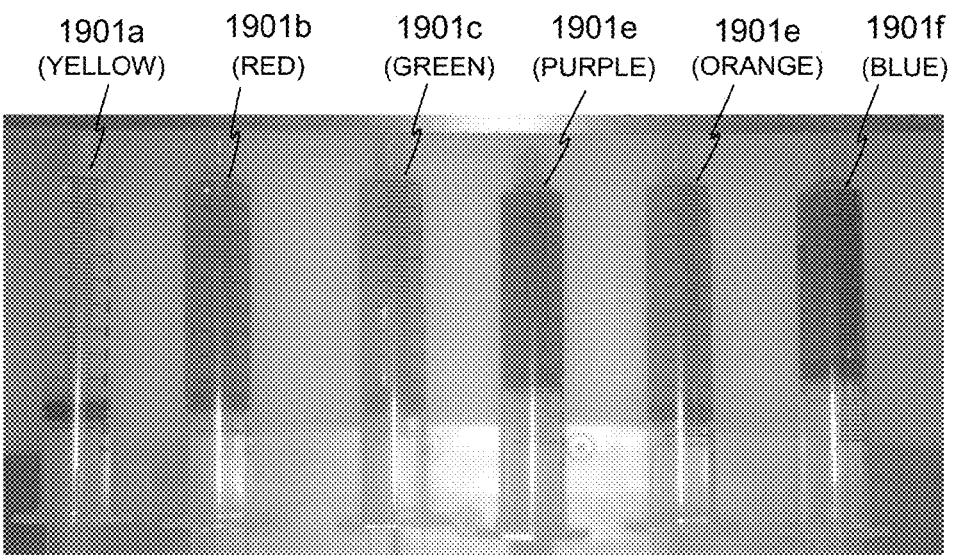
FIG. 19 shows an example photograph of a number of syringes, as may be taken by a visible light camera in accordance with embodiments of the invention.

FIG. 19 shows an example photograph of a number of syringes 1901*a*-1901*f* as may be taken by visible light camera 403 using light sources 405. Each of syringes 1901*a*-1901*f* contains fluid of a different color. Although the fluids in FIG. 19 are not necessarily pharmaceuticals, FIG. 19 illustrates that visible light camera 403 can distinguish a wide range of colors, and a photograph taken with visible light camera 403 may enable a pharmacist to verify that a compounded liquid is of an expected color, bolstering confidence that the compounding was done correctly, or to detect that a compounded liquid is not of the expected color, indicating that the compounding may not have been done correctly.

Figure 20:
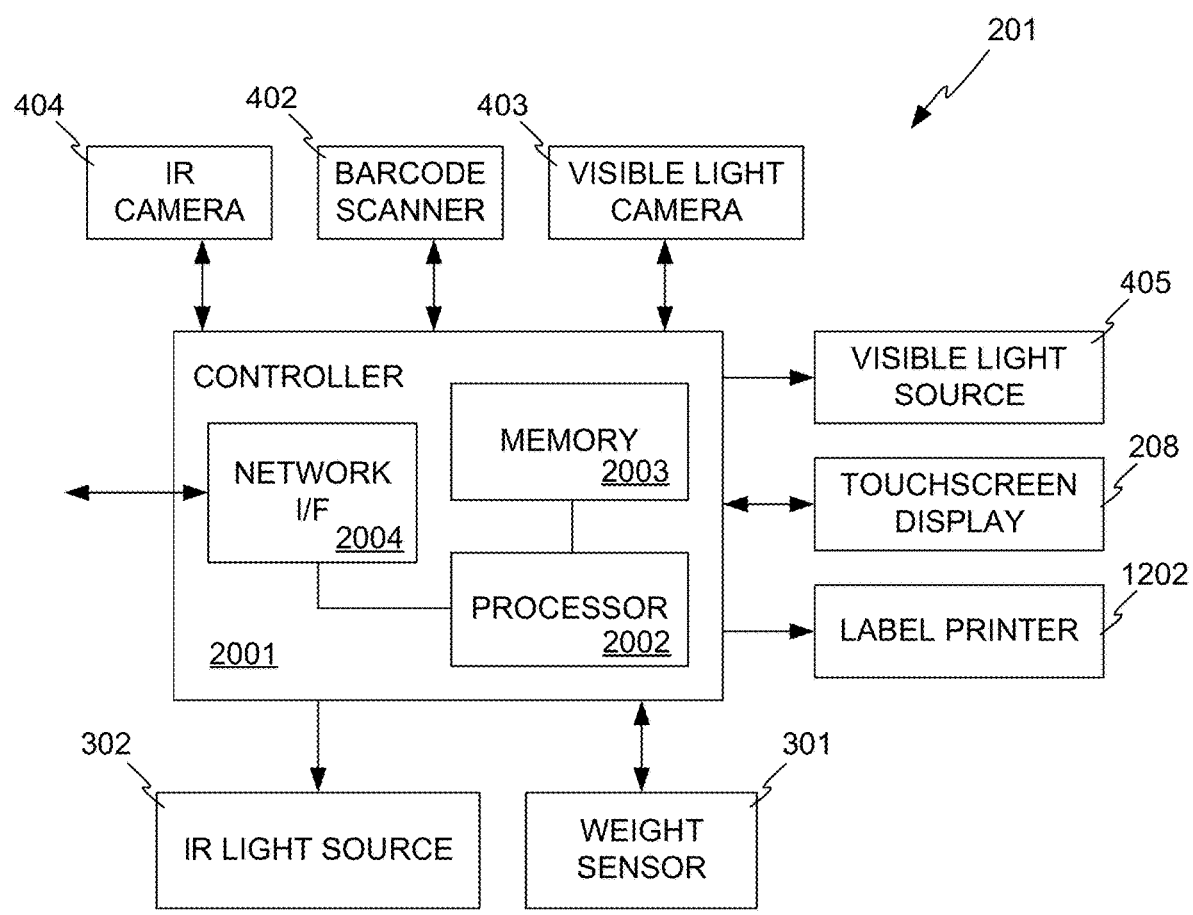
FIG. 20 illustrates a simplified block diagram of the compounding assistance device of FIG. 3, in accordance with embodiments of the invention.

FIG. 20 illustrates a simplified block diagram of compounding assistance device 201, in accordance with embodiments of the invention. Compounding assistance device 201 includes a controller 2001 comprising a processor 2002, memory 2003, and a network interface 2004. Memory 2003 may include dynamic memory, non-volatile memory, mass storage, or other kinds of memory in any suitable combination. Part of memory 2003 holds instructions for processor 2002 that, when executed, control the operation of compounding assistance device 201. Other kinds of information may be stored in memory 2003 as well, for example working copies of digital images, temporary variables, and other kinds of information. Network interface 2004 allows controller 2001 to communication externally, for example with a server such as pharmacy server 101 described above.

Compounding assistance device 201 further includes infrared camera 404, barcode scanner 402, and visible light camera 403 as described above, all in communication with controller 2001 and under the control of controller 2001. Infrared light source 302 and visible light source 405 are also under the control of controller 2001, to be turned on and off at different times. In some embodiments, the intensity of the light produced by either or both light sources may be adjustable under the control of controller 2001. Touchscreen display 208 can communicate information to a user of compounding assistance device 201, and can receive instructions from the user.

Label printer 1303 receives commands and data from controller 2001 for the printing of labels. Weight sensor 301 provides signals to controller 2001 indicating the weight of tray 209 and any items on it.

Other architectures for compounding assistance device 201 may be used.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. It is to be understood that any workable combination of the elements and features disclosed herein is also considered to be disclosed.

The invention has now been described in detail for the purposes of clarity and understanding. However, those skilled in the art will appreciate that certain changes and modifications may be practiced within the scope of the appended claims.

What is claimed is:

1. A compounding assistance device, comprising:
   a carrier for supporting items, wherein the material of the carrier is not opaque to infrared light;
   an infrared digital camera positioned to photograph at least a portion of the carrier from above;
   an area light source positioned under the carrier, the area light source configured to generate infrared light and direct the infrared light through the carrier and toward the infrared digital camera;
   a display;
   a controller programmed to guide a user of the compounding assistance device through a pharmaceutical compounding task using one or more prompts shown on the display;
   a visible light digital camera positioned to photograph at least a portion of the carrier from above;
   a source of visible light positioned adjacent the visible light digital camera and controllable by the controller to emit light during taking of a photograph using the visible light digital camera;
   a bar code scanner positioned to read a bar code from an item between the bar code scanner and the carrier; and
   a gantry spanning the carrier;
   wherein the infrared and visible light digital cameras, the bar code scanner, and the visible light source are mounted on the gantry.

2. The compounding assistance device of claim 1, further comprising a weight sensor on which the carrier rests, the weight sensor configured to produce a signal indicating the weight of the carrier and any items on the carrier.

3. The compounding assistance device of claim 1, wherein the visible light digital camera is a color digital camera.

4. The compounding assistance device of claim 1, wherein the area light source under the carrier comprises:
   a plurality of infrared light emitting diodes; and
   a diffuser.

5. The compounding assistance device of claim 1, wherein:
   the area light source under the carrier comprises a plurality of infrared light emitting diodes; and
   the carrier is made of a diffusing material.

6. The compounding assistance device of claim 1, further comprising an adhesive label printer, wherein the controller is programmed to, upon completion of the pharmaceutical compounding task, print an adhesive label to be affixed to a container holding the pharmaceutical compounded during the compounding task.

7. The compounding assistance device of claim 1, wherein the controller is further programmed to:
   analyze a digital photograph of a syringe taken in infrared light by the infrared digital camera; and estimate an amount of liquid in the syringe based on the analysis of the digital photograph.

8. The compounding assistance device of claim 1, wherein the carrier defines a groove of a shape and size for receiving a barrel flange of a syringe.

9. The compounding assistance device of claim 1, wherein the controller is further programmed to:
   analyze a digital photograph of a syringe taken in infrared light by the infrared digital camera;
   recognize a size of the syringe based on the analysis of the digital photograph; and
   annotate the digital photograph of the syringe with volume indications.

10. A pharmaceutical compounding device, comprising:
    a gantry spanning a carrier;
    an infrared area light source;
    an infrared digital camera;
    a visible light digital camera;
    a source of visible light positioned adjacent the visible light digital camera;
    a viewing area between the infrared area light source and the infrared digital camera;
    a bar code scanner positioned to read a bar code from an item between the bar code scanner and the carrier; and
    a controller programmed to control the infrared area light source and the infrared digital camera to take a first photograph of an item in the viewing area such that the item is backlit by the infrared area light source, and to take a second photograph of the viewing area using the visible light digital camera, and to control the source of visible light:
    wherein the infrared and visible light digital cameras, the bar code scanner, and the visible light source are mounted on the gantry.

11. The pharmaceutical compounding device of claim 10, wherein:
    the pharmaceutical compounding device is a compounding assistance device comprising a display; and
    the controller is further programmed to guide a user of the device through a compounding task using prompts shown on the display.

12. The pharmaceutical compounding device of claim 10, wherein the pharmaceutical compounding device is a compounding robot.

* * * * *

UNITED STATES PATENT AND TRADEMARK OFFICE
CERTIFICATE OF CORRECTION

PATENT NO. : 10,991,264 B2
APPLICATION NO. : 15/865038
DATED : April 27, 2021
INVENTOR(S) : Giuseppe Trovato, Andrea Schiavinato and Luca Amato It is certified that error appears in the above-identified patent and that said Letters Patent is hereby corrected as shown below:

On the Title Page

Column 1, Item (30), Under Foreign Application Priority Data:
Delete "IT2017134813" and insert -- 102017000134813 --.

In the Specification

Column 9, Line 11:
Delete "302," and insert -- 302. --.

In the Claims

Claim 10, Column 14, Line 9:
Delete "...using the visible light digital camera, and to control the source of visible light:" and insert
-- "...using the visible light digital camera, and to control the source of visible light;" --.

Signed and Sealed this
Twelfth Day of November, 2024

Katherine Kelly Vidal
*Director of the United States Patent and Trademark Office*